(12) United States Patent
Kitada et al.

(10) Patent No.: US 6,586,648 B2
(45) Date of Patent: Jul. 1, 2003

(54) PROCESS FOR PRODUCING CYCLOPENTADIENE OR DERIVATIVES THEREOF AND APPARATUS FOR THE SAME, AND PROCESS FOR PRODUCING METALLOCENES OR DERIVATIVES THEREOF

(75) Inventors: Katsutsugu Kitada, Kanagawa (JP); Hiroaki Suzuki, Kanagawa (JP)

(73) Assignee: Tanaka Kikinzoku Kogyo K.K., Tokyo (JP)

( * ) Notice: Subject to any disclaimer, the term of this patent is extended or adjusted under 35 U.S.C. 154(b) by 113 days.

(21) Appl. No.: 09/822,413

(22) Filed: Apr. 2, 2001

(65) Prior Publication Data

US 2001/0047120 A1 Nov. 29, 2001

(30) Foreign Application Priority Data

Apr. 28, 2000 (JP) ........................................ 2000-128699

(51) Int. Cl.⁷ .......................... C07C 5/31; C07F 15/00; C07F 17/00; C23C 16/00
(52) U.S. Cl. ........................ 585/354; 556/136; 427/593
(58) Field of Search .................... 585/354; 556/136; 427/593

(56) References Cited

U.S. PATENT DOCUMENTS 3,590,089 A * 6/1971 Robota ........................ 585/354

* cited by examiner

*Primary Examiner*—Porfirio Nazario-Gonzalez
(74) *Attorney, Agent, or Firm*—Rothwell Figg Ernst & Manbeck

(57) ABSTRACT

The present invention provides a process for producing cyclopentadiene or a derivative thereof by heating a mixture containing at least one of dicyclopentadiene or a derivative thereof, the process comprising: a first step comprising heating the mixture into vapor; a second step comprising maintaining while heating the vapor at a temperature higher than the boiling point of the desired cyclopentadiene or derivative thereof to condense and remove high-boiling components and simultaneously collect residual vapor; and a third step comprising maintaining while heating the collected vapor at a temperature lower than the boiling point of the desired cyclopentadiene or derivative thereof to condense and collect the cyclopentadiene or derivative thereof. In the third step, the vapor may be contact with nitrogen gas to improve the yield of the cyclopentadiene or derivative thereof.

6 Claims, 2 Drawing Sheets

PROCESS FOR PRODUCING CYCLOPENTADIENE OR DERIVATIVES THEREOF AND APPARATUS FOR THE SAME, AND PROCESS FOR PRODUCING METALLOCENES OR DERIVATIVES THEREOF

BACKGROUND OF THE INVENTION

1. Field of the Invention

The present invention relates to a process for producing cyclopentadiene or a derivative thereof usable as a raw material of an organic metal compound for use as a source material for CVD and to an apparatus for the process. The present invention also relates to a process for producing an organic metal compound using the cyclopentadiene or derivative thereof produced by the process.

2. Description of the Related Art

Chemical vapor deposition (hereinafter, referred to as "CVD") can provide a uniform film and is good in step coverage, and therefore recently has been widely applied in a process for producing a circuit board or a thin film electrode for an electronic component for which higher density is required.

The source materials used for CVD are organic metal compounds which have lower melting temperatures and are easier to handle than other metal compounds. Typical organic metal compounds widely applicable as CVD source materials are metallocenes (i.e., biscyclopentadienyl metal complexes) represented by formula (1) and derivative thereof having a functional group (e.g., a hydrocarbon, amino, carboxyl or ether group) introduced to one or both of the hydrogen moieties on the cyclopentadiene rings. In particular, the latter metallocene derivatives have been expected as potential source materials for CVD, because they have high vapor pressures and also have properties suitable as source materials for CVD.

Formula (1)

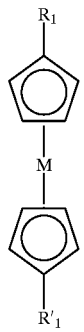

wherein each of substituents $R_1$ and $R'_1$ is a hydrogen atom or at least one of substituents $R_1$ and $R'_1$ is a hydrocarbon, amino, carboxyl or ether group; and M represents a metal atom.

The metallocene and derivative thereof have a sandwich structure in which a metal atom is sandwiched between two cyclopentadiene rings. As is apparent from the structural formula above, the metallocene has been produced by reacting cyclopentadiene with a metal compound (e.g., a chloride, a calbonylated compound). The metallocene derivative has been produced by reacting a cyclopentadiene derivative into which a functional group is previously introduced with a metal compound.

On the other hand, cyclopentadiene and a derivative thereof have the property of readily causing dimerization at a temperature around room temperature. Therefore, in general, for the production of a metallocene or a derivative thereof, dimeric dicyclopentadiene or a dimeric dicyclopentadiene derivative is thermally decomposed into monomers and then provided to the reaction for the production of the metallocene or derivative thereof.

SUMMARY OF THE INVENTION

However, the dimers as the raw materials of the cyclopentadiene or derivative thereof may contain an impurity or impurities, although in a small amount. If a dimer of such impurity-containing cyclopentadiene or derivative thereof is thermally decomposed, the resulting cyclopentadiene or cyclopentadiene derivative may also contain an impurity or impurities.

Particularly, a cyclopentadiene derivative has been produced by first reacting cyclopentadiene with metal sodium to produce a cyclopentadiene-type anion and then introducing a functional group to the anion. In this case, cyclopentadiene is usually added in an excess amount in view of the safety during operation. Hence, dimerization between the cyclopentadiene derivative product and the unreacted cyclopentadiene may occur to produce a dimer as an adverse by-product, which may be contained in the cyclopentadiene derivative. Moreover, in this production process, an undesired cyclopentadiene derivative to which a larger number of the functional groups than required are introduced or an unintended functional group is introduced may also be contained. Accordingly, when the reaction product is thermally decomposed, unreacted cyclopentadiene or an unexpected cyclopentadiene derivative may be contained as an impurity in the cyclopentadiene derivative product.

The use of a monomer of such impurity-containing cyclopentadiene or cyclopentadiene derivative may inevitably lead to low purity of the resulting metallocene or metallocene derivative.

A source material for CVD is required to be highly pure for ensuring satisfactory electrical properties as a thin film. Accordingly, when a metallocene or a derivative thereof with low purity is used as the source material, it is required to remove an impurity or impurities. However, once a metallocene or metallocene derivative is formed, such purification is quite difficult because physical properties among the produced metallocene derivatives are similar to each other. For these reasons, it is necessary to provide a cyclopentadiene monomer of high purity for the production of a metallocene of high purity.

Under these situations, the present invention has been developed. Accordingly, the object of the present invention is to provide a process for producing cyclopentadiene or a derivative thereof with high purity for use in the production of a metallocene or metallocene derivative with high purity as a source material of CVD and to provide an apparatus for the process. Another object of the present invention is to provide a process for producing a metallocene or a metallocene derivative using cyclopentadiene or a derivative thereof produced by the process.

In order to solving the problems as mentioned above, the present inventors made studies on the purification of cyclopentadiene or a cyclopentadiene derivative which is a monomer produced after the thermal decomposition of a dimeric form thereof. However, the inventors concluded that the removal of an impurity or impurities in this state is not practical, because the amount of the impurity or impurities contained in the product is very small. Then, the inventors have considered that only a desired monomer could be removed during the thermal decomposition of the dimer so that the production and purification of the monomer can be performed simultaneously and, consequently, monomeric cyclopentadiene or cyclopentadiene derivative of high purity could be produced with good efficiency. This consideration led to the accomplishment of the present invention.

The present invention provides a process for producing cyclopentadiene or a derivative thereof by heating a mixture containing dicyclopentadiene or a derivative thereof represented by formula (2) to produce cyclopentadiene or a derivative thereof represented by formula (3), the process comprising: a first step comprising heating the mixture into vapor; a second step comprising maintaining while heating the vapor at a temperature higher than the boiling point of the desired cyclopentadiene or derivative thereof to thereby condense and remove a high-boiling component(s) and simultaneously collect the residual vapor; and a third step comprising maintaining while heating the collected vapor at a temperature lower than the boiling point of the desired cyclopentadiene or derivative thereof to thereby condense and collect the cyclopentadiene or derivative thereof:
Formula (2)

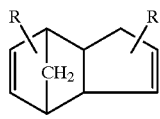

wherein each substituent group R represents a hydrogen atom or a hydrocarbon, amino, carboxyl or ether group;
Formula (3)

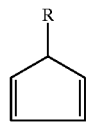

wherein a substituent group R is as defined above.

The present invention is characterized in that two temperature ranges are selected around the boiling point of desired cyclopentadiene or derivative thereof and the vapor of a monomer which is produced by thermal decomposition of a dimeric compound is subjected to two-stage distillation treatment within the two temperature ranges, so that the thermal decomposition of the dimeric compound and the removal of an impurity or impurities from the resulting monomeric products can be achieved simultaneously. That is, in the distillation process under high temperature of step 2 performed after the thermal decomposition of step 1, an impurity or impurities having a boiling point higher than that of the desired cyclopentadiene (herein, also referred to as "high-boiling impurity or impurities") are heated at a temperature lower than the boiling point of the cyclopentadiene and condensed. Since the impurity or impurities can be removed in this manner, only the desired cyclopentadiene and an impurity or impurities having a lower boiling point than that of the cyclopentadiene (herein, also referred to as "low-boiling impurity or impurities") are contained in the residual vapor. In the distillation process in step 3, the cyclopentadiene is heated at a temperature lower than the boiling point of its own and condensed. By collecting the condensed component, a cyclopentadiene of high purity can be obtained.

As mentioned above, in the present invention, impurities having wide range of boiling points can be removed by the two-stage distillation. Therefore, according to the present invention, only desired cyclopentadiene or derivative thereof can be extracted with satisfactory purity.

The process of the present invention is a combination of conventional thermal decomposition of a dicyclopentadiene (i.e., a production process for a cyclopentadiene) and conventional purification of the cyclopentadiene. According to the present invention, the production and purification of cyclopentadiene can be performed simultaneously, and therefore the production of cyclopentadiene or a derivative thereof can be achieved at low cost with good production efficiency.

With respect to the heating temperature for the distillation in each step, when the boiling point of the cyclopentadiene or derivative thereof to be produced is represented by $T_b$ (° C.), the temperature at which the vapor is maintained while heating in the second step is represented by $T_1$ (° C.) and the temperature at which the vapor is maintained while heating in the third step is represented by $T_2$ (° C.), $T_1$ and $T_2$ are adjusted so that the following relationships can be held:

$T_1 = T_b + 10$;

$T_2 \leq 20$ (in the case where the desired product is cyclopentadiene);

$T_2 = 50$ (in the case where the desired product is a cyclopentadiene derivative).

The reason for the adjustment of $T_1$ and $T_2$ as defined above is as follows. With respect to $T_1$, if $T_1$ is too low, then the desired cyclopentadiene or derivative thereof may also be condensed. This is not desirable since step 2 is for condensation of only a high-boiling impurity or impurities. If the temperature $T_1$ is too high, then the resulting monomeric compound may cause polymerization. With respect to $T_2$, $T_2$ is varied depending on the form of the desired product (i.e., cyclopentadiene or a derivative thereof). When the desired product is cyclopentadiene, $T_2$ is set at a temperature not higher than 20° C. for the purpose of preventing the dimerization of the cyclopentadiene which can readily occur at a temperature around room temperature. When the desired product is a cyclopentadiene derivative, $T_2$ is set at 50° C. In this case, since cyclopentadiene is also included in undesirable impurities, this temperature is convenient for removal of low-boiling impurities including the cyclopentadiene.

In step 3, it is desirable to contact the residual vapor with inert gas for the purpose of improving the yield of the desired cyclopentadiene. The contact with inert gas can accelerate the evaporation of the low-boiling impurities in the vapor and promote the separation of the cyclopentadiene or derivative thereof from the impurity or impurities. The inert gas usable in this step includes nitrogen, argon and so on.

The cyclopentadiene or cyclopentadiene derivative produced by the process according to the present invention as described above is a highly pure product free from any impurity and therefore is useful as a raw material of a metallocene or metallocene derivative. The process for producing the cyclopentadiene or derivative thereof of the present invention can be performed by an apparatus having a relatively simple configuration.

The apparatus essentially comprises: a reaction vessel for containing a mixture containing dicyclopentadiene or a derivative thereof; first heating means for heating the reaction vessel to vaporize the mixture; second heating means for heating the vapor to a temperature higher than the boiling point of the desired cyclopentadiene or derivative thereof; separation means for separating the vapor heated by the second heating means into a condensed component(s) and residual vapor; third heating means for heating the residual vapor separated by the separation means to a temperature lower than the boiling point of the desired cyclopentadiene or derivative thereof; and a collecting vessel for collecting a condensed component(s) generated from the residual vapor heated by the third heating means, wherein the reaction vessel, the separation means and the collecting vessel are connected through a series of piping means.

The first heating means may include a hot bath, an electrical heater, a heat exchanger and so on. The second and third heating means may include an electric heater and a heat exchanger. The type of each heating means may be suitably selected depending on the amount of the cyclopentadiene or derivative thereof to be produced. As for the separation means for separating the heated mixture into a condensed component(s) (i.e., a high-boiling impurity or impurities) and vapor (i.e., a mixture of the cyclopentadiene or derivative thereof and a low-boiling impurity or impurities), various fractionating columns may be applied for a laboratory scale production and industrial-scale apparatuses (e.g., a distilling column, a packed column) may be applied in the case where the amount of the product is increased.

In the apparatus for producing cyclopentadiene or a derivative thereof according to the present invention, it is desirable to provide a condenser for cooling and condensing the vapor generated by the third heating means (i.e., a low-boiling impurity or impurities) and a cold trap which is provided downstream to the condenser, in addition to the devices as mentioned above. These two components can serve to remove the low-boiling impurity or impurities from the exhaust gas.

As mentioned above, it is preferable to contact the vapor with nitrogen gas for the purpose of promoting the separation of the cyclopentadiene from the low-boiling impurity or impurities and improving the yield of the cyclopentadiene. Accordingly, in the apparatus for producing cyclopentadiene or a derivative thereof according to the present invention, it is preferable to provide nitrogen gas supply means to the piping means for allowing the contact of the vapor heated by the third heating means to with nitrogen gas.

The cyclopentadiene or derivative thereof produced by the process or apparatus according to the present invention may be reacted with a metal compound to produce a metallocene of high purity. The production of a metallocene will be described hereinbelow.

The production of a metallocene may be performed by several methods, such as a method in which cyclopentadiene or a derivative thereof is reacted with a metal chloride $(MCl_n)$ in an alcohol solvent together with zinc powder, a method in which cyclopentadiene or a derivative thereof is reacted with a metal carbonyl $[M(CO)_n]$ by heating to 250 to 300° C., and a method in which cyclopentadiene or a derivative thereof is reacted with a metal halide $(MX_n)$ in the presence of a base. The cyclopentadiene or derivative thereof produced according to the present invention can be applied to any method.

The metal species which constitutes the metallocene is not particularly limited, and metallocene complexes of various metals, such as ferrocene (Fe), titanocene (Ti) and chromocene (Cr), can be produced. In recent years, use of a thin film of a noble metal (e.g., ruthenium, platinum and iridium) as a thin film electrode has been focused, and therefore the application of a metallocene complex of a precious metal as a source material for CVD has been studied. The cyclopentadiene or derivative thereof produced according to the present invention can be applied to the production of metallocene complexes of noble metals and can produce noble metal metallocenes of high purities. Since noble metals are very rare metals, the present invention can help the efficient utilization of such rare metals.

BEST MODE FOR CARRYING OUT THE INVENTION

Hereinbelow, the preferred embodiments of the present invention will be described with reference to the drawings.

Figure 1:
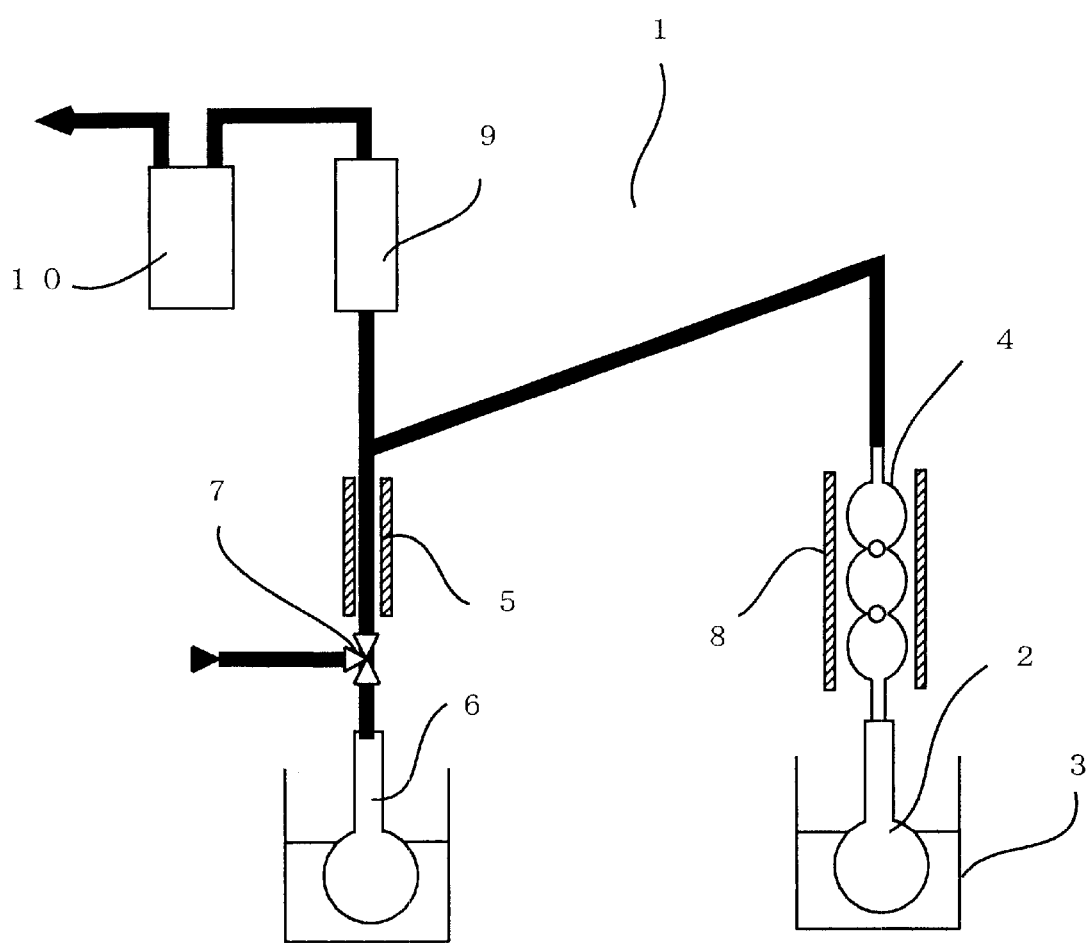
FIG. 1 shows the constitution of an apparatus for producing cyclopentadiene or a derivative thereof used in Examples 1 to 3.

FIG. 1 is a schematic illustration of the constitution of an apparatus 1 for producing cyclopentadiene or a derivative thereof used in the embodiments. As shown in FIG. 1, the apparatus 1 comprises a reaction vessel 2 for containing dicyclopentadiene or a derivative thereof; a hot bath 3 as first heating means; a fractionating column 4 for separating vapor from the reaction vessel 2; a heating column 5 for heating vapor separated by the fractionating column 4 as third heating means; and a collecting vessel 6 for collecting the condensed cyclopentadiene or derivative thereof. A valve 7 is provided on a pipeline between the heating column 5 and the collecting vessel 6 for supplying nitrogen gas. As second heating means, a heater 8 is provided surrounding the fractionating column 4 for maintaining the fractionating column 4 under heated condition. On the side of a gas exhaust port, a condenser 9 and a cold trap 10 are provided.

In the production of cyclopentadiene or a derivative thereof using the apparatus, the reaction vessel 2 is heated by elevating the temperature of the hot bath 3 to a temperature higher than the decomposition temperature of the dicyclopentadiene or derivative thereof. Vapor generated by the heating passes through the fractionating column 4, while a low-boiling impurity or impurities which is heated by the heater 8 to a temperature higher than the boiling point of the desired cyclopentadiene or derivative thereof are condensed and removed. The vapor without the high-boiling impurity or impurities is then heated to a temperature lower than the boiling point of the desired cyclopentadiene or derivative thereof through a boiling column 5. During this process, the desired cyclopentadiene or derivative thereof is condensed and collected in the collecting vessel 6. On the other hand, the residual vapor, which contains only an impurity or impurities having a boiling point lower than that of the desired cyclopentadiene or derivative thereof, passes through the condenser 9, whereby only the low-boiling impurity or impurities is condensed and collected in the cold trap 10.

Cyclopentadiene and derivatives thereof were produced using the apparatus 1 as follows.

EXAMPLE 1

Production of Cyclopentadiene

Dicyclopentadiene (800 g) was charged in a reaction vessel 2. The temperatures of a hot bath 3 and a heater 8 were set to 150° C. and 80° C., respectively. Each temperature of a heating column 5 and a condenser 9 was maintained at room temperature. Nitrogen gas was supplied from a nitrogen gas supply inlet at 1000 ml/min.

As a result, monomeric cyclopentadiene (570 g) was produced. The purity of the monomeric cyclopentadiene was determined and found to be as extremely high as 99.98%.

EXAMPLE 2

Production of Methyl Cyclopentadiene

In this example, methyl cyclopentadiene ($R=CH_3$) was produced as a cyclopentadiene derivative. A dimer of methyl cyclopentadiene (800 g) was charged in a reaction vessel 2. The temperatures of a hot bath 3 and a heater 8 were set to 180° C. and 70° C., respectively. Both temperatures of a heating column 5 and a condenser 9 were set to 50° C. Nitrogen gas was supplied from a nitrogen gas supply inlet at 1000 ml/min.

As a result, monomeric methyl cyclopentadiene (570 g) was produced. The purity of the monomeric methyl cyclopentadiene was determined and found to be as extremely high as 99.8%.

EXAMPLE 3

Production of Ethyl Cyclopentadiene

In this example, ethyl cyclopentadiene ($R=C_2H_5$) was produced as a cyclopentadiene derivative. A dimer of ethyl cyclopentadiene (800 g) was charged in a reaction vessel 2. The temperatures of a hot bath 3 and a heater 8 were set to 200° C. and 90° C., respectively. Both temperatures of a heating column 5 and a condenser 9 were set to 50° C. Nitrogen gas was supplied from a nitrogen gas supply inlet at 1000 ml/min.

As a result, monomeric ethyl cyclopentadiene (570 g) was produced. The purity of the monomeric ethyl cyclopentadiene was determined and found to be as extremely high as 99.5%.

Comparative Example 1

In order to assess the purities of the cyclopentadiene and so on produced by the apparatus for producing a cyclopentadiene derivative according to the present invention, a dimer of ethyl cyclopentadiene was thermally decomposed by a conventional thermal decomposition apparatus to produce ethyl cyclopentadiene.

Figure 2:
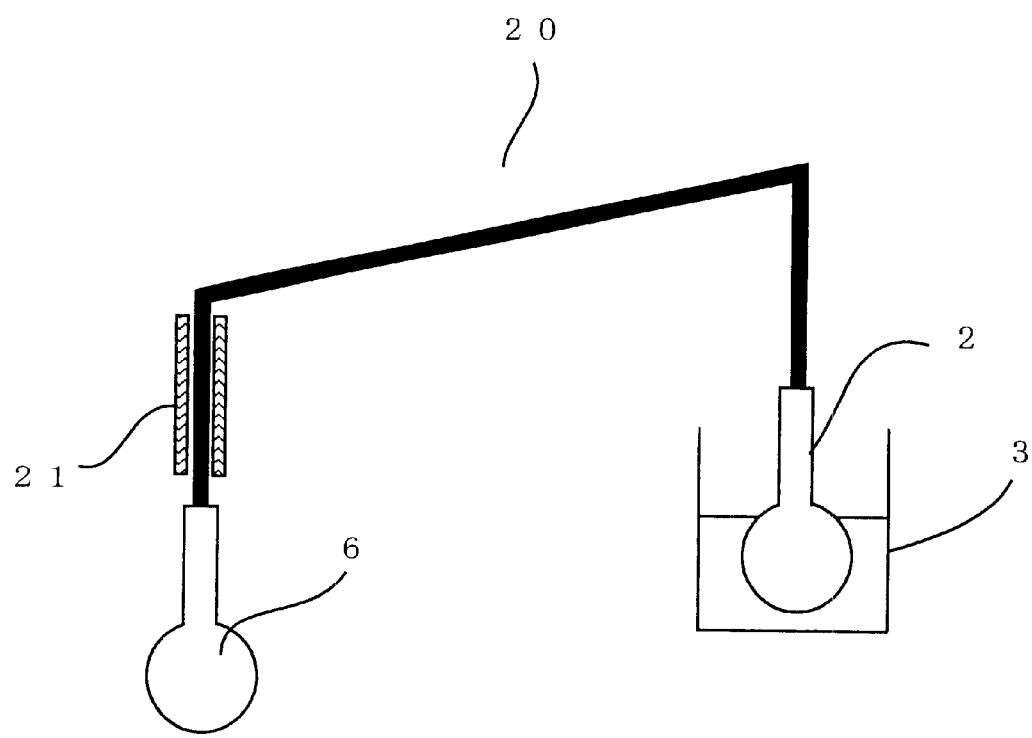
FIG. 2 shows the constitution of an apparatus (a thermal decomposition apparatus) for producing cyclopentadiene or a derivative thereof used in Comparative Example.

In FIG. 2, the configuration of a thermal decomposition apparatus 20 used in Comparative Examples is shown. As shown in FIG. 2, the thermal decomposition apparatus 20 comprises: a hot bath 3 for heating a reaction vessel 2 to a temperature higher than the boiling point of ethyl cyclopentadiene; and a collecting vessel 6 for collecting ethyl cyclopentadiene. A cooling column 21 for condensing the ethyl cyclopentadiene is provided in the upper part of the collecting vessel 6.

Ethyl cyclopentadiene was produced with the thermal decomposition apparatus 20. A dimer of ethyl cyclopentadiene (800 g) was charged in a reaction vessel 2. The temperatures of a hot bath 3 and a cooling column 21 were set to 200° C. and 20 ° C., respectively. The dimer of ethyl cyclopentadiene was thermally decomposed under these conditions. As a result, monomeric ethyl cyclopentadiene (440 g) was produced. The purity of the monomeric ethyl cyclopentadiene was determined and found to be 91.2%, which is lower than that of the ethyl cyclopentadiene produced in Example 3.

EXAMPLE 4

Production of Bis(Methyl Cyclopentadienyl) Ruthenium

Next, bis(methyl cyclopentadienyl)ruthenium, which has a methyl group introduced to each of the two cyclopentadiene rings, was produced as a derivative of ruthenocene using the methyl cyclopentadiene produced in Example 2.

Ruthenium chloride (1000 g) was mixed with ethyl alcohol (3000 ml) and stirred at −20° C. for 3 hours. The methyl cyclopentadiene (3500 ml) produced in Example 2 and zinc powder (3000 g) was added to the mixed solution and then allowed to react at room temperature for 96 hours. After the reaction was completed, the reaction solution was extracted with benzene and the solvent was then evaporated, thereby yielding bis(methyl cyclopentadienyl)ruthenium (1000 g). The purity of the bis(methyl cyclopentadienyl)ruthenium was determined and found to be as extremely high as 99.8%.

EXAMPLE 5

Production of Bis(Ethyl Cyclopentadienyl) Ruthenium

Bis(ethyl cyclopentadienyl)ruthenium, which has an ethyl group introduced to each of the two cyclopentadiene rings, was produced as a derivative of ruthenocene using the ethyl cyclopentadiene produced in Example 3.

Ruthenium chloride (1000 g) was mixed with ethyl alcohol (3000 ml) and stirred at −30° C. for 3 hours. The ethyl cyclopentadiene (3500 ml) produced in Example 3 was added to the mixed solution, zinc powder (3000 g) was further added dividedly thereto over 7 times, and then allowed to react at −25° C. for 24 hours. After the reaction was completed, the reaction solution was extracted with hexane and the solvent was then evaporated, thereby yielding bis(ethyl cyclopentadienyl)ruthenium (1000 g). The purity of the bis(ethyl cyclopentadienyl)ruthenium was determined and found to be as extremely high as 99.5%.

Comparative Example 2

Bis(ethyl cyclopentadienyl)ruthenium was produced using the ethyl cyclopentadiene produced in Comparative Example 1.

Ruthenium chloride (250 g) was mixed with ethyl alcohol (2000 ml) and stirred at −30° C. for 3 hours. The ethyl cyclopentadiene (400 ml) produced in Comparative Example 1 was added to the mixed solution, zinc powder (670 g) was further added dividedly thereto over 7 times, and then allowed to react at −25° C. for 24 hours. After the reaction was completed, the reaction solution was extracted with hexane and the solvent was distilled off, thereby yielding bis(ethyl cyclopentadienyl)ruthenium (190 g). The purity of the bis(ethyl cyclopentadienyl)ruthenium was determined and found to be as low as 94.5%. The difference in concentration of bis(ethyl cyclopentadienyl)ruthenium between the product in Comparative Example 2 and the product in Example 5 is merely the order of several %. However, when these products are used as source materials for CVD, such a small difference in concentration may lead the contamination of a finished thin film or a CVD device.

What is claimed is:

1. A process for producing cyclopentadiene or a derivative thereof by heating at least one compound which is dicyclopentadiene or a derivative thereof represented by formula (1) to produce cyclopentadiene or a derivative thereof represented by formula (2), the process comprising:

a first step comprising heating the compound into vapor;

a second step comprising maintaining while heating the vapor at a temperature higher than the boiling point of the desired cyclopentadiene or a derivative thereof to thereby condense and remove high boiling components and simultaneously collect residual vapor; and a third step comprising removing low boiling impurities from the collected residual vapor by maintaining while heating the collected vapor at a temperature lower than the boiling point of the desired cyclopentadiene or derivative thereof to thereby condense and collect the cyclopentadiene or derivative thereof without condensing low boiling impurities:

Formula (1)

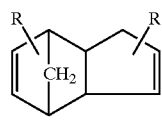

wherein a substituent group R represents a hydrogen atom, or a hydrocarbon, amino, carboxyl or ether group;

Formula (2)

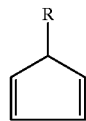

wherein a substituent group R is as defined above.

2. The process for producing cyclopentadiene or a derivative thereof according to claim 1, wherein, when the boiling point of the desired cyclopentadiene or derivative thereof is represented by $T_b$ (° C.), the temperature at which the vapor is maintained while heating in the second step is represented by $T_1$ (° C.) and the temperature at which the vapor is maintained while heating in the third step is represented by $T_2$ (° C.), $T_1$ and $T_2$ are adjusted so that the following relationships can be held:

$T_1 = T_b + 10$;

$T_2 = 50$ (in the case where the desired product is a cyclopentadiene derivative);

$T_2 \leq 20$ (in the case where the desired product is cyclopentadiene).

3. The process for producing cyclopentadiene or a derivative thereof according to claim 1, wherein the vapor is contacted with nitrogen gas in the third step.

4. Cyclopentadiene or a derivative thereof having a purity of 99% or more as produced by the process according to claim 1, wherein the cyclopentadiene is substantially free from low boiling impurities.

5. The process for producing cyclopentadiene or a derivative thereof according to claim 1, wherein the vapor is contacted with an inert gas in the third step.

6. The process for producing cyclopentadiene or a derivative thereof according to claim 5, wherein the inert gas is argon.

* * * * *